(12) United States Patent
Ozkul et al.

(10) Patent No.: US 8,746,077 B2
(45) Date of Patent: Jun. 10, 2014

(54) WIRELESS ENABLED FATIGUE SENSOR FOR STRUCTURAL HEALTH MONITORING

(75) Inventors: Tarik Ozkul, Istanbul (TR); Halit Kaplan, Balgat (TR); Melik Dolen, Cayyolu (TR)

(73) Assignee: Tarik Ozkul, Istanbul (TR)

( * ) Notice: Subject to any disclaimer, the term of this patent is extended or adjusted under 35 U.S.C. 154(b) by 269 days.

(21) Appl. No.: 13/320,937

(22) PCT Filed: Jan. 16, 2010

(86) PCT No.: PCT/IB2010/050203
§ 371 (c)(1),
(2), (4) Date: Nov. 17, 2011

(87) PCT Pub. No.: WO2011/086427
PCT Pub. Date: Jul. 21, 2011

(65) Prior Publication Data
US 2012/0060621 A1    Mar. 15, 2012

(51) Int. Cl.
*G01N 3/32* (2006.01)
(52) U.S. Cl.
USPC .............................. 73/810; 73/830
(58) Field of Classification Search
USPC .................. 73/810, 821, 830, 834–835, 845
See application file for complete search history.

(56) References Cited

U.S. PATENT DOCUMENTS

| | | | | | |
|---|---|---|---|---|---|
| 4,030,348 | A * | 6/1977 | Fletcher et al. | .................. | 73/809 |
| 4,676,110 | A * | 6/1987 | Hodo et al. | ..................... | 73/809 |
| 5,355,734 | A * | 10/1994 | Kajino | ............................ | 73/775 |
| 5,528,151 | A * | 6/1996 | Perez | ............................ | 324/525 |
| 7,621,193 | B2 * | 11/2009 | Fay et al. | ..................... | 73/865.9 |
| 7,719,416 | B2 * | 5/2010 | Arms et al. | ................. | 340/539.1 |
| 8,138,773 | B2 * | 3/2012 | Fay et al. | ..................... | 324/700 |

FOREIGN PATENT DOCUMENTS

JP         2007315810 A    12/2007

* cited by examiner

*Primary Examiner* — Max Noori
(74) *Attorney, Agent, or Firm* — Cesari and McKenna, LLP (57) ABSTRACT

A fatigue sensor for monitoring the health state of structural members is disclosed. The sensor has multiple parallel beams, each sensitive to different levels of fatigue, that are designed to fail prematurely but progressively as the sensor goes through the same fatigue cycles as the structural member it is attached to. Whenever fatigue levels on a particular beam of the sensor exceed the engineered number of fatigue cycles, that particular beam fails and sensor electronics can detect that failure and transmit this information wirelessly when interrogated by an external interrogator. Having multiple beams that fail after different numbers of fatigue cycles enables the health state of the structural member to be monitored, in that unlike normal fracture sensor that sense failure of the structural members after the actual fracture event, the present invention is capable of sensing imminent failure of the structural member before the actual failure occurs.

18 Claims, 6 Drawing Sheets

WIRELESS ENABLED FATIGUE SENSOR FOR STRUCTURAL HEALTH MONITORING

CROSS REFERENCE TO RELATED APPLICATIONS

This application is the national stage entry under 35 USC 371 for PCT/IB2010/050203, filed Jan. 16, 2010. The contents of the foregoing application is incorporated herein by reference.

FIELD

This application is related testing structures. It is further related to investigating elasticity of structures for monitoring their integrity over time in the service. Its practical use will be for monitoring health state of structural members of an aircraft or components of a bridge.

BACKGROUND

Failures that are caused by the fatigue loads on the structural parts could be followed by fatal accidents. Mechanical parts can fail unexpectedly due to fatigue loads and result in loss in life and property. Several fatigue design techniques have been developed in order to bring a solution to this problem. The best-known method is the ASME holistic design methodology. In this methodology, during the design phase, working conditions are taken into consideration so that fatigued design is operational for a specific lifetime. However, this model does not guarantee that mechanical parts would work under the assumed conditions or stay undamaged during the assumed lifetime of the structure. Hence, fatigue failure has been a problem and leads to fatal accidents in a variety of mechanical parts.

Observing real-time fatigue damage is important in order to set up a correct balance between performance and structural integrity of mechanical systems. Several methods have been developed to detect fatigue damage on critical mechanical parts and structural elements working under cyclic loads. In model analysis technique, obtaining information about fatigue damage is possible by observing the variations of frequency and vibration models, originated by cracks in the mechanical parts. Another technique to determine the damages resulted by the stress concentrations is wave propagation. In this method, the response of the original system is observed in the frequency domain and the values are compared to the fatigued version of the system to reveal fatigue damage. Yet another method is based on measuring stress values synchronously on critical points of the structure (such as in the joints of aircraft wings) and therefore projecting fatigue effects that are resulted by these.

It is utmost critical to monitor structural integrity of safety-critical structures like bridges, aircraft, naval ship etc. as they age in service. Failure to do so results in catastrophic failure of the structure during its service life, which may cause damage to lives and property. Performing manual inspection of structures by human inspectors is not only difficult but also proved to be unsatisfactory as it is easy to miss problem spots. Because of its importance, there have been many research and countless inventions toward this subject in the literature.

Boller and Meyendorf reviewed the state of the art in structural health monitoring in an article titled "State of the art in structural health monitoring for aeronautics" in 2008 in Proceedings of International Symposium on NDT (non destructive testing) in Aerospace. The article lists state of the art of sensors used for aircraft health monitoring applications and lists sensors like; electrical strain gauges, electrical crack wires, acoustic emission, acousto-ultrasonics, laser vibrometry, comparative vacuum monitoring (CVM), optical fiber Bragg grating (FBG), MEMS and electromagnetic foils. These sensors are designed toward sensing existence of the cracks that develop during lifetime of the structure.

Another review report is published by L. Fixter and C. Williamson titled "State of the art Review—Structural Health Monitoring" includes additional sensors used for monitoring bridge and civil structures as well as structures like aircraft. Yet another up-to-date article published by Papazian et al. in issue 29 of Journal of Fatigue, dated 2007, titled "Sensors for monitoring early stage fatigue cracking" explains use of eddy current, ultrasonic sensor and electrochemical fatigue sensor (EFS) in detail. These sensors also detect cracks that develop during life time of the structure.

There are also many commercially available fatigue sensors in the market. B. M. Phares from Material Technologies, Inc. reviews one of the innovative sensors called electrochemical fatigue sensor in a technology review article titled "The electrochemical fatigue sensor: A novel sensor for active fatigue crack detection and characterization" which is available from companies' website.

There have been numerous patent applications for sensors that detect health state of structures. U.S. Pat. No. 7,621,193 B2 by Fay et al. is a patent titled "Fracture detecting structural health sensor" which works by attaching a frangible membrane including a thin conductor sense loop is connected to a structural element to be tested. Failure of the structural element destroys the thin conductor sense loop and reveals the failure of the structural member. This invention is also designed to detect the crack after the crack occurs. The crack developed on the surface of the structure destroys the frangible loop and the sensor senses the existence of the crack this way.

Another patent application US 2009/031 by Goldfine et al. titled "Primary windings having multiple parallel extended portions" uses series of eddy current sensors to detect not only the existence but also the size of the crack developing under the sensor attached surface. Like the previous patent, this invention is also geared toward detecting cracks after the crack develops. As the crack progressively gets longer, more and more eddy current sensors sense the situation and inform the status of the crack Majority of the sensors mentioned above, regardless whether they are chemical, optical, or electrical, they are all designed toward detecting the existence of the cracks. In the present invention, the approach is different. Rather than detecting the existence of the crack, the present invention intends to estimate the remaining service life of the structure and raise an alarm when the service life of the structural member gets closer to its limit. The sensor is wireless enabled which makes it possible to check the status of the sensor easily through as sensor network.

Reading sensors wirelessly is a well-researched subject and its techniques are well known in the state of the art. Lei et al. published an article in Chinese Journal of Aeronautics in 2009 in issue 22 titled, "Design an Experiment of PCT Network-Based Structural Health Monitoring Scanning System" explaining how such a wireless network can be constructed. Another article published by Mascerenas et al. titled, "Experimental Studies of Using Wireless Energy Transmission for Powering Embedded Sensor Nodes" in 2009 issue of the Journal of Sound and Vibration to describe how remote sensors with no batteries can be powered by remote RF energy in a bridge monitoring application.

Structural health monitoring applications requires a robust, reliable and easy to read sensors to monitor the fatigue state of structural members. What the expectations should be from an ideal structural health monitoring systems is researched by researchers from industry and academia. J. D. Acenbach summarizes these expectations in a review article titled "Structural health monitoring—What is the prescription?" in Journal of Mechanics Research Communications, 36 (2009) 137-142 as follows;

An ideal Structural Health Monitoring system should have such features:
Should have permanently installed microsensors,
On demand or continuous condition monitoring in real time should be possible,
Wireless transmission to central station,
Instantaneous interpretation of sensor data,
Detection of unacceptable material damage at critical high-stress locations,
Monitoring of growth of material damage into critical size,
Growth prediction by a probabilistic procedure,
Adjustments to growth prediction for actual damage state at prescribed intervals,
Probabilistic forecast of damage state for near term and of lifetime.
Incorporation of all these attributes into a single structural health monitoring is not likely, but these are the desired features of from a state of the art, ideal structural health monitoring system.

Additionally, there are many technical challenges for ideal sensors to overcome. Ideally, the sensors used in structural health monitoring systems should be:
Small (microsensors), ligthweight.
Autonomously powered without any power wires,
Cheap, robust, maintainable, repairable and easy to install,
Accurate, known probability of detecting failure (POD).
Easy to properly couple to structure without causing any damage,
Suitable for wireless transmission to central station,
Can be densely distributed,
Capable of measuring both local and system-level response,
Designed to measure relevant damage parameters.

The above requirements are summary of expectations from ideal structural health monitoring sensors. The present invention intends to address some of these requirements to come up with a lightweight, reliable sensor which enables monitoring health state of the structure whether it is an aircraft or a bridge.

SUMMARY

The present invention is a fatigue sensor with multiple parallel beams designed to sense different levels of fatigue cycles all integrated into a single sensor. The sensor is designed to be attached to a structural member of the structure which undergoes continues cyclic bending like a wing of an aircraft or beam of a bridge.

The sensor has multiple beams and each beam of the sensor has an engineered geometry with a strategically shaped and placed notch. Because of the notch placement, the fatigue affects on the beam are concentrated to a specific portion of the beam. The sensor is supposed to be attached to a structural member that goes through repeated cyclic bending process. As the sensor goes through the cyclic bending process, the beams inside the sensor are subjected to accelerated fatigue process and fail well before the structural member it has been attached to fails. Because of its engineered geometry, notch placement and notch size, the failure time of the beams are highly predictable. The beams inside the sensor are designed fail at different fatigue cycles so as to give progressive, advanced warning about the health state of the structural member.

Figure 1:
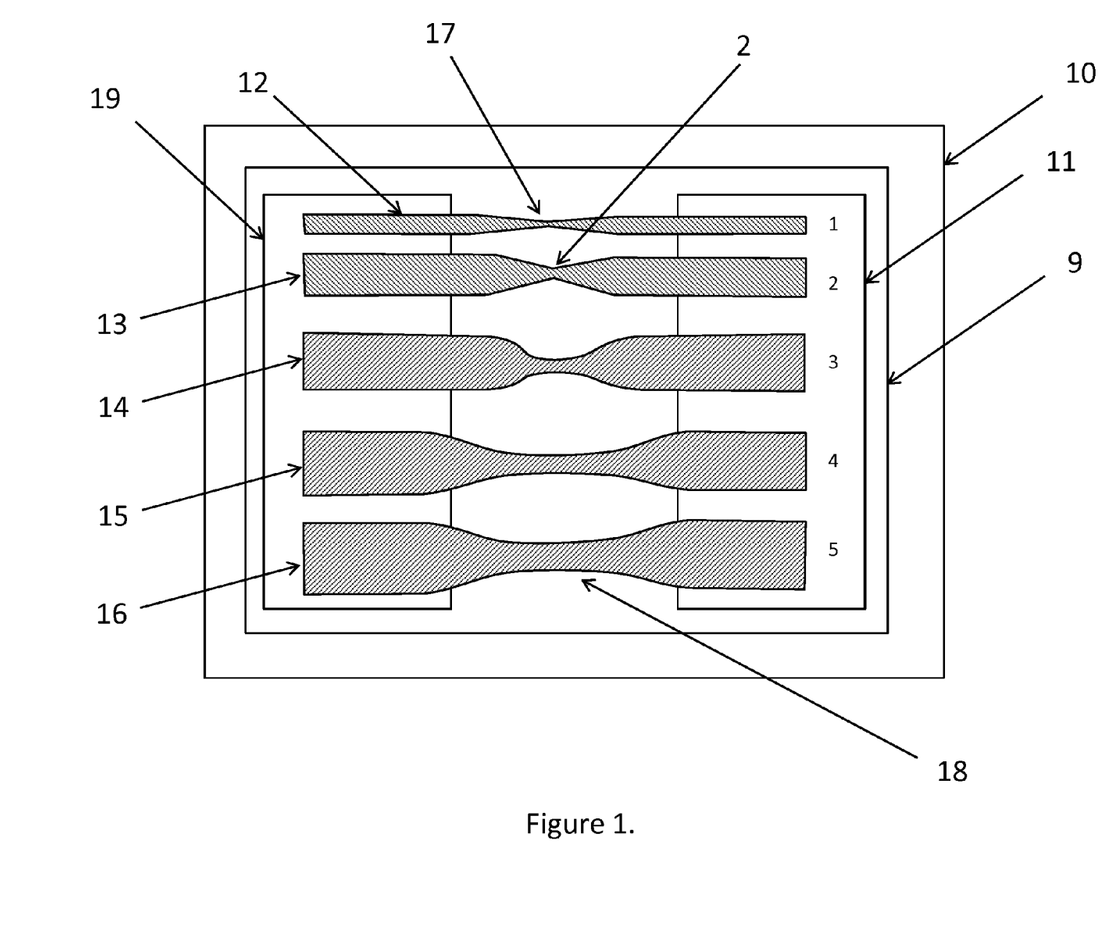
FIG. 1 General view of the fatigue sensor.

Let us explain the concept with an example. As an example, in one embodiment of the invention, the beams of the sensor shown in FIG. 1 are designed to fail at different fatigue cycles. Beam 1 is designed to have a lifetime of 10,000 cycles, beam 2 is engineered to have a life cycle of $1 \times 10^6$ cycles, beam 3 is engineered to have a lifetime of $10 \times 10^6$, beam 4 is engineered to have a lifetime of $50 \times 10^6$ and beam 5 is engineered to have a lifetime of $90 \times 10^6$ cycles.

In a structural health-monitoring scenario, suppose this sensor is attached to a structural member that has life expectancy of $100 \times 10^6$ cycles. During the service life of the structure, the attached sensor starts going through the same fatigue cycle as the structural member. After only 10,000 cycles the beam 1 of the sensor fails. Beam 1 is deliberately designed to fail at a very early stage of the service life of the structural member just to indicate that sensor is properly attached to the structural member and going through the fatigue cycles properly. The sensor is wireless enabled, so it can be interrogated wirelessly through an appropriate, long range RFID reader or through a wireless sensor network. In a typical scenario, the sensor either has a long life battery which drains power only when it is interrogated or has no battery and powered by the RF (radio frequency) signal sent by the RFID reader. Interrogation of the sensor reveals the number of beams failed inside the sensor and gives an idea about the remaining service life of the structural member. By interrogating the sensor at regular service intervals, we can monitor both the health of the sensor and the structural member. In the scenario presented above, failure of beam number 4 should alert the responsible people about servicing the structure. Failure of beam number 5 should ring alarm bells about the health status of the structure.

The present invention uses beams engineered with special geometry and notch placement to predict the fatigue cycle of beams inside the sensor. Prediction of fatigue cycle of notched beams is well researched in the literature and well-known in the current state of the art. Some of the articles related to this part of the state of the art can be listed as follows;

A. M. Eleciche, et al. "Low Cycle Fatigue and Rotating Cantilever under Bending. III: Experimental Investigations on Notched Specimens" International Journal of Fatigue, 28 (2006) 271-280.

L. Susmel et al. "Non-Propagating Cracks and High Cycle Fatigue Failures in Sharply Notched Specimens under in-phase Mode I and II loading" Engineering Failure Analysis, 14 (2007) 861-876.

S. Laue et al. "Spectrum fatigue life assessment of notched specimens based on the initiation and propagation of short cracks", 28 (2006) 1011-1021.

The present invention combines these known states of the art for development of a predictive fatigue sensor that intends to predict the remaining service life of structures.

DESCRIPTION

The operation of the fatigue sensor will now be described using figures. The present invention is a fatigue sensor comprising beams and associated electronics. FIG. 1 shows the beam structure inside the sensor 10, which constitutes the actual sensing part. In this particular embodiment, the sensing process is done by the beams 12, 13, 14, 15 and 16, which are made from a material with known fatigue characteristics. In one embodiment of the invention, beams 12, 13, 14, 15, and 16 may also be manufactured from the same base material as the structural member it is intended to monitor its health. Yet in another particular embodiment of the design may use aluminum as the material of choice for fabrication of the beams. Beams 12, 13, 14, 15, 16 are mounted on rigid plates 11 and 19 supporting both sides of the beams 12, 13, 14, 15, 16. Due to rigid nature of the bases 11 and 19, any movement of these rigid base plates is transferred to beams 12, 13, 14, 15, and 16 exactly the same way. This ensures all beams 12, 13, 14, 15, 16 experience the same fatigue movement simultaneously. Item marked as 9 is a thin layer of insulating material intended to insulate sensor electrically from the structural member it is attached to. This insulating material 9 is a compliant material and does not dampen the movement of the structural member. The fatigue movement of the structural member is transferred to rigid base plates 11 and 19 of the sensor.

Beams 12, 13, 14, 15, 16 may have different width, thickness and notch size placed on them. The notch size 2, notch shape 18, width and thickness of the beam are parameters that determine the fatigue life of each beam. Since each beam is designed to have a different fatigue life, these parameters are engineered for each beam. How the calculation of these parameters is done for the desired fatigue life of the beam is well known in the state of the art which is reviewed in the background part of this document.

Figure 2:
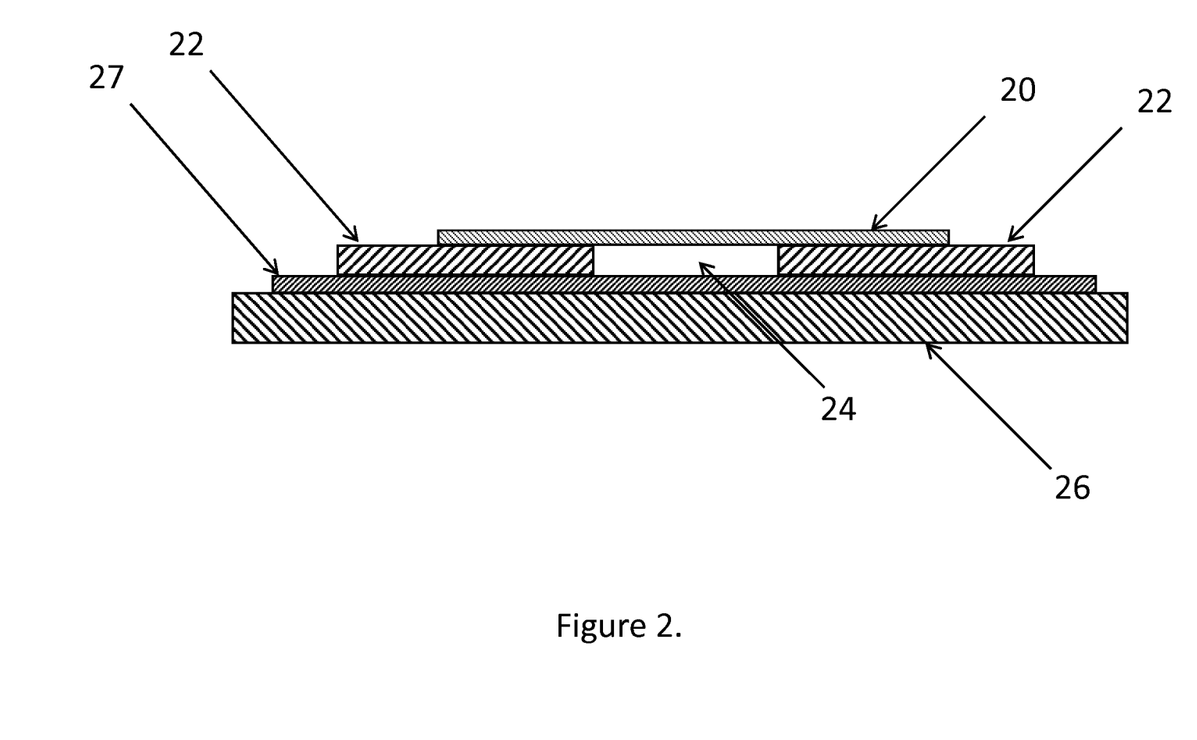
FIG. 2 Side view of the fatigue sensor.

FIG. 2 shows the side view of the one of beams inside the sensor. Beam 20 is mounted on two rigid plates 22 supporting both sides of the beam. There is a gap 24 between the rigid base plates of the sensor. The beams bend in this gap particularly at the notch point. A thin insulating layer 27 electrically isolates beams from the structural member. Sensor is supposed to be attached to a structural member 26 of the structure by the rigid plates 22. One embodiment of the sensor may use adhesives to attach rigid plates 22 to structural member 26.

Figure 3:
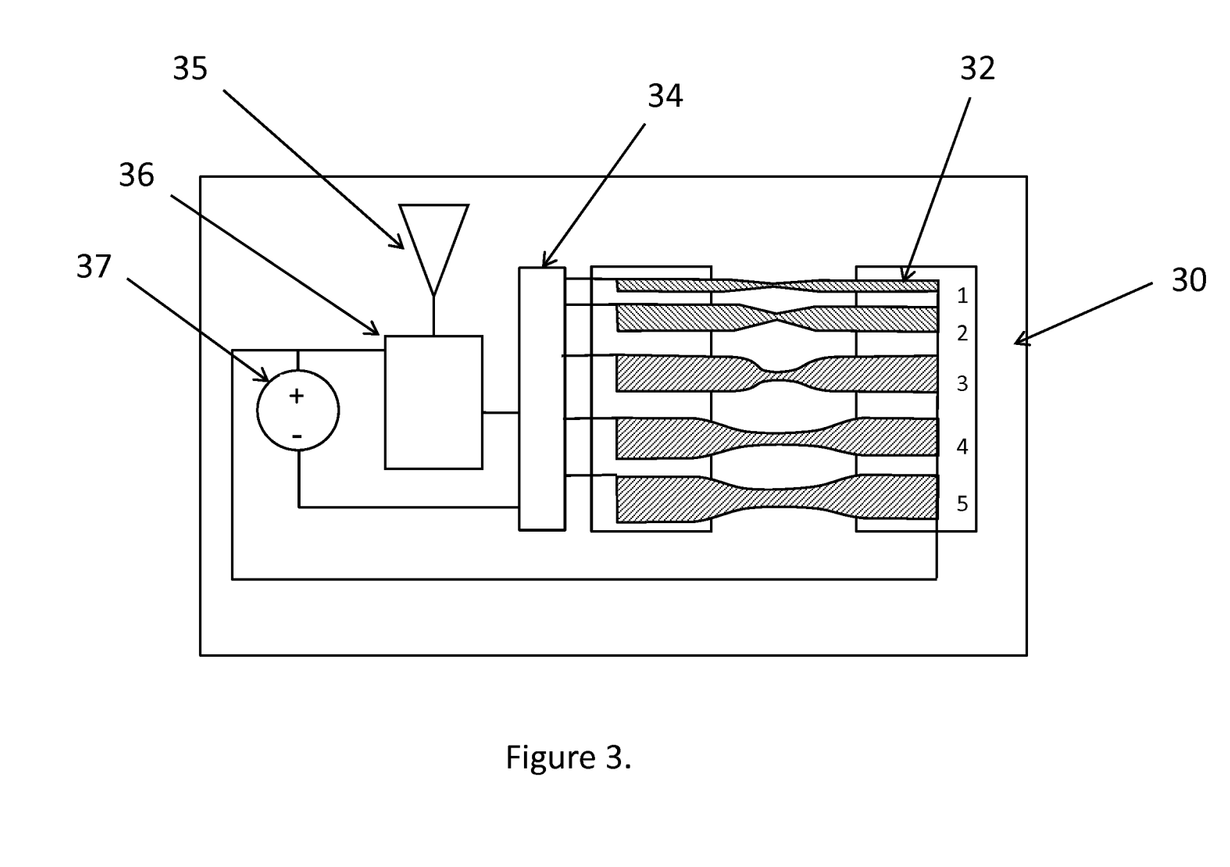
FIG. 3 Fatigue sensor with electronic parts.

FIG. 3 shows the sensor with the associated control electronics. Electronics part of the sensor comprises power source 37, controller 36, input port 34 and transmitter unit 35. Power source 37 may be a battery, or a capacitor or a power harvesting unit or a coil to convert RF energy to power to energize the sensor electronics. Controller 36 contains a digital processor to read sensor state from input port 34, encode this information digitally, and put it into an information package suitable for transmission. The information package may also contain a digital identification number distinguishing each sensor distinctively. In one embodiment of the invention, the controller 36 may an RFID tag like METALuCID tag manufactured by MBBS SA corporation which can transmit information through metal plates as thick as 1 mm of metal. In another embodiment of the invention, the controller 36 may be a wireless sensor node like a ZigBee end node operating with low power radio transmission principles as dictated in IEEE 802.15.4 standard. In such a case, the controller 36 transmits sensor information along with its identification code to the surrounding ZigBee router nodes or the ZigBee coordinator node interrogating the other nodes. The state of the art regarding designing low power radio networks is very well know by professionals who are experienced in this aspect of the network design.

Transmitter unit 35 comprises the antenna and the related electronics necessary for wireless transmission. In one embodiment of the invention, the transmitter unit 35 may be an optical transmitter transmitting information through light waves. In another embodiment, 35 may be the transmitter coil of an RFID tag, or in another embodiment it may the antenna of a low power wireless network.

Power source 37 may be either a battery or a capacitor or a power harvester unit to provide energy for this particular node. Providing power through externally transmitted RF energy is a well-known technique for providing short-term energy to remote nodes that have no batteries. The technique is well known by the professionals practicing this art and related reference for such method is given in the background part of this document. In such an embodiment, the power source 37 may be a coil and associated electronics designed for this purpose.

Input port 34 is a simple digital input port to read switch status from the beams. Beams 32 are electrically conductive and normally all non-failed beams provide a digital logic "0" signal at the input port 34. Any failed beam becomes non conductive and its state appears as logic "1" at the input port 34 which will be read by controller 36 and eventually transmitted by antenna 35.

Figure 4:
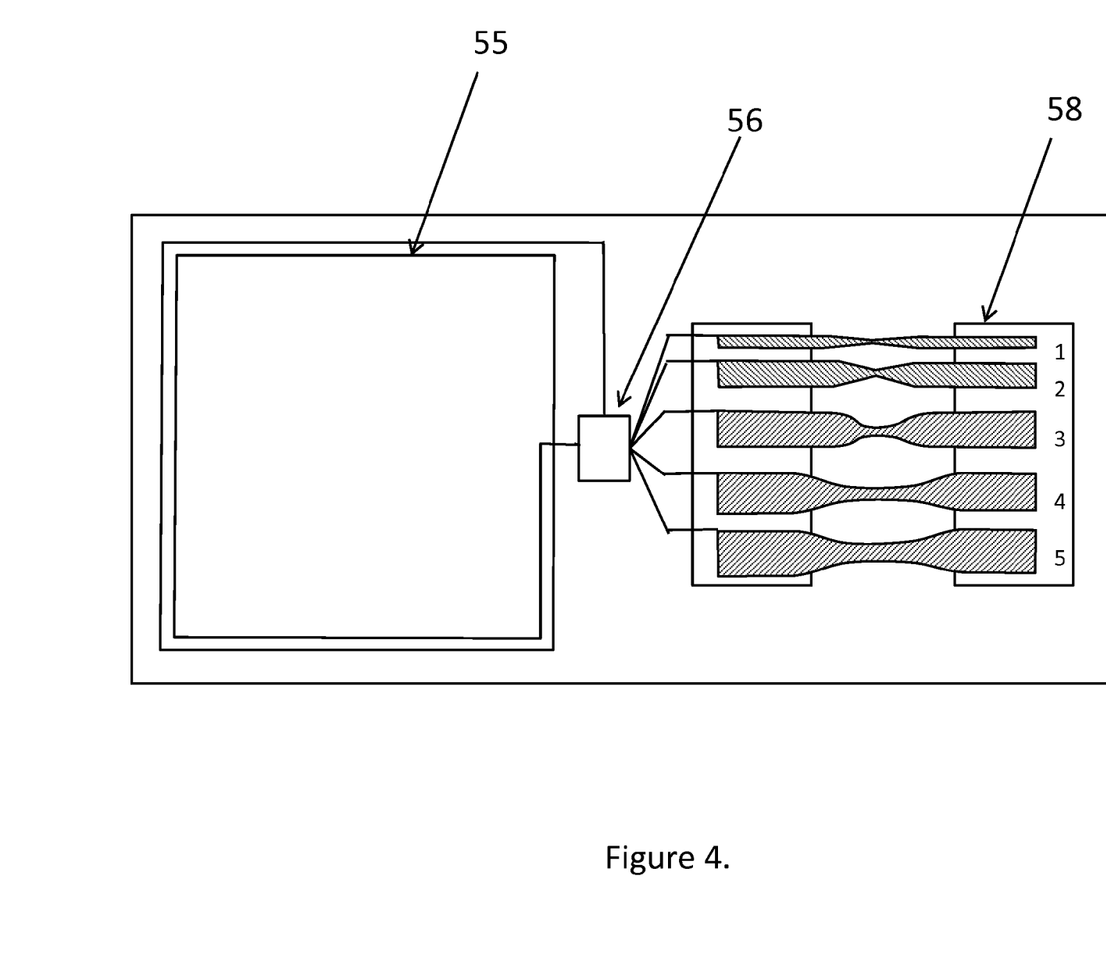
FIG. 4 A particular embodiment of the sensor with no battery.

FIG. 4 shows a particular embodiment of the invention manufactured using typical high power RFID technology. Current state of the art allows manufacture of controller in micro scale which can be in dimensions of several millimeters and take only minute space on the sensor board. In this particular embodiment, the power source is the coil 55 that converts externally transmitted RF energy to electrical power needed to power the controller 56 that reads and transmit state of the sensor beams 58. The state of the art in high power RFID transmission is well known by practitioners' and it is widely being used in RFID tags for collecting toll for highway or bridges.

Figure 5:
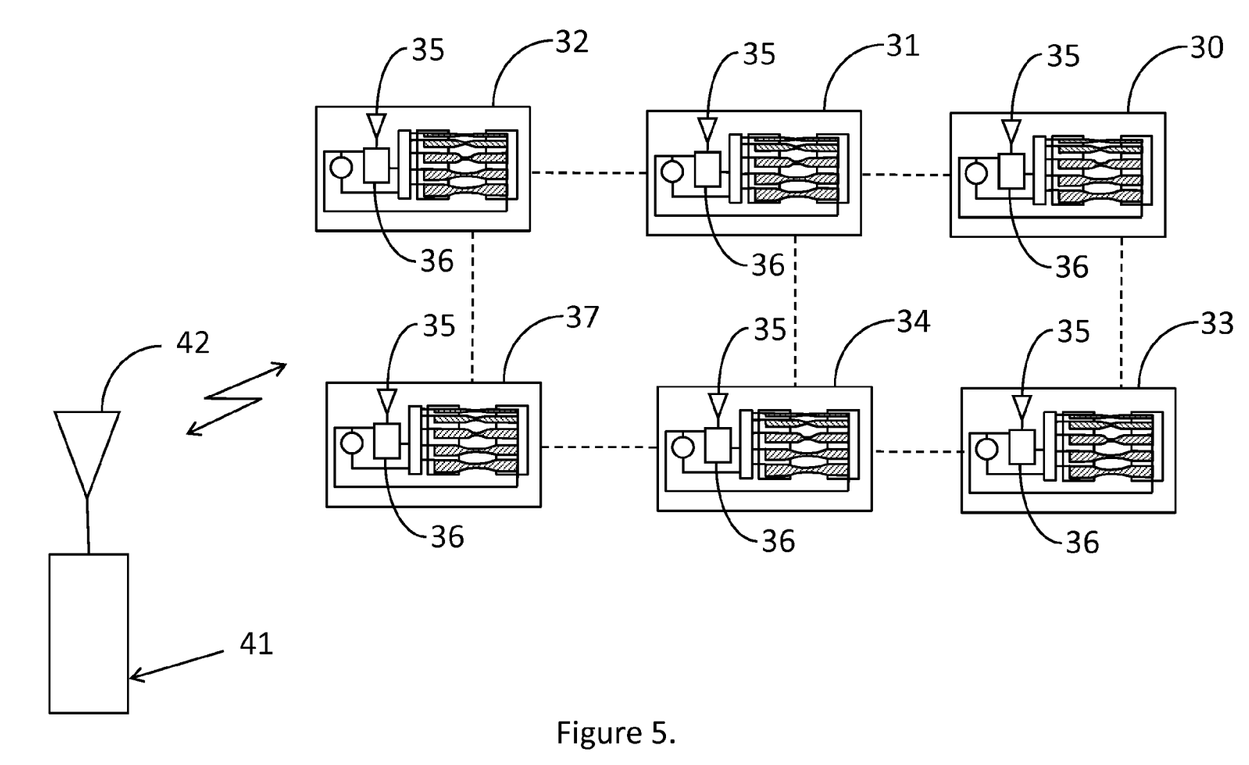
FIG. 5 Operation of multiple sensor nodes.

FIG. 5 shows a particular embodiment of the design where the sensor nodes are arranged in a low power network like IEEE 802.15.4 standard network. In such a case, the sensor nodes 30 are scattered around the structure and an external interrogator 41 is being used for collecting information from the sensor nodes. Sensor node 37 may be close to interrogator 41 and relay its information. Sensor node 30 may be far away from interrogator and can not hear the transmission. In such a case, the information is relayed by other nodes in between, like node 34, which can communicate both with node 30 and interrogator 41. The state of the art in this type of network is well known by the practitioners who practice wireless sensor network design.

FIG. 5 also can be used to explain operation of RFID based sensor cluster. In such an embodiment, 41 is the interrogator which is a high power RFID transmitter that can send high power RF waves through it is antenna 42 to energize sensor nodes 30, 31, 32, 33, 34 and 37 and interrogate each sensor about the state of the beams inside the sensor.

Figure 6:
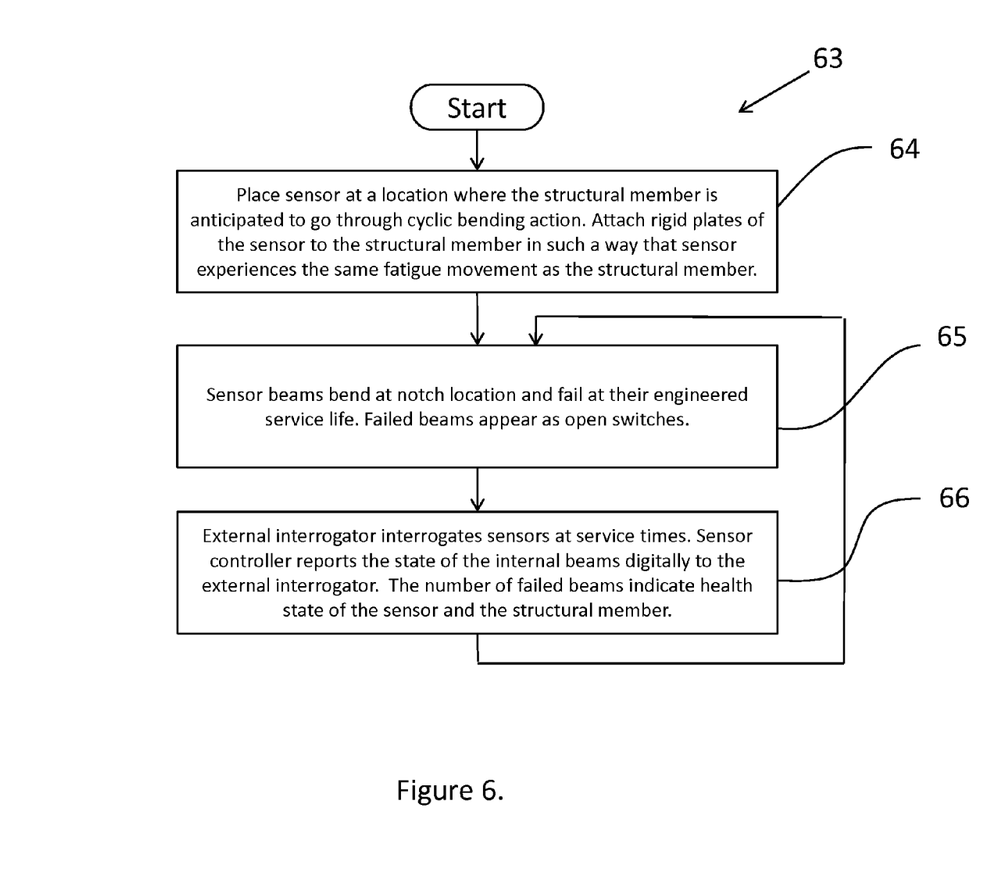
FIG. 6 Flowchart of the operation of the sensor.

The method of using invention is described with the aid of FIG. 6. The 63 is the process flow chart, which describes the sensing process. In 64, the sensor is attached to a suitable location of the structural member, which undergoes the fatigue cycle. Being attached rigidly to the structural member, the sensor also goes through the same fatigue cycle as the structural member is going through. In 65, the beams inside the sensor start failing consecutively as they go through the repeated bending cycles. In 66, the external interrogator interrogates the sensor during service intervals to read the status of beams inside the sensor. The number of beams failed inside the sensor indicates the health status of the sensor and the structural beam it is attached to. The external interrogation process is repeated at different service times and health status of structure is monitored progressively. As the structure ages, the beams inside the sensor expires one by one and as the number of remaining beams reduced, the structural member is supposed to be serviced or replaced.

The beams inside the sensor may be engineered to last different number of lifecycles as per requirement of the structure that is being monitored.

The invention claimed is:

1. A sensor for monitoring a health status of a structural member of a structure, comprising:
   a plurality of breakable beams;
   electronics configured to sense broken beams and to wirelessly transmit information indicating broken beams; and
   a power source to power the sensor, the sensor deployed on or near the structural member of the structure and configured to monitor the health status of the structural member by undergoing a same repetitive cyclic bending movement as the structural member.

2. The apparatus of claim 1, wherein said plurality of breakable beams of said sensor are made from a same material as said structural member or from a different material with known fatigue characteristics and organized in parallel, or radial, or in such a way that all said breakable beams are subjected to the same repetitive cyclic bending movement as the structural member.

3. The apparatus of claim 1, wherein said breakable beams are manufactured with notches of varying size and shape to go through an accelerated fatigue process due to said repetitive cyclic bending movement and to break after a different number of bending movements in a progressive manner well before said structural member to which it has been attached fails.

4. The apparatus of claim 3, wherein said breakable beams are manufactured with notches of different size or placement or another similarly engineered beam geometry to concentrate stress on a particular area of said beams and to make a failure time of each individual beam highly predictable.

5. The apparatus of claim 1, wherein the electronics includes a processor.

6. The apparatus of claim 1, wherein said power source to the sensor comprises a battery, a capacitor, externally provided RF signal power, or other means of energy harvesting techniques, or a combination of said parts to power the sensor.

7. The apparatus of claim 1, wherein said electronics provide information indicative of the broken beams to a processor electrically, or optically in digital or analog fashion.

8. The apparatus of claim 1, wherein said plurality of breakable beams are attached to two rigid base plates, wherein each rigid base plate supports one side of said beams.

9. The apparatus of claim 8, wherein said rigid base plates are bonded to a structural member surface and are between the structural member surface and a second structural member surface.

10. A method of sensing a structural health status of a structural member comprising:
    deploying a sensor with a plurality of breakable sensing beams onto the structural member, the sensing beams configured to undergo a same repetitive cyclic movement as the structural member
    and to break progressively after undergoing a different number of repetitive cyclic bending movements due to fatigue built up on the beams; and
    sensing broken sensing beams electrically, optically or by other means and transmitting information indicative of the broken sensing beams to an external or internal interrogator at requested service intervals.

11. The method of claim 10, wherein the breakable sensing beams are made from a same material as the structural member, or a different material with known fatigue characteristics so as to give an indication of a fatigue status of said structural member to which the breakable sensing beams are deployed onto.

12. The method of claim 10, wherein one side of said sensor is bonded to a first surface of said structural member and the other side of said sensor is bonded to a second surface of said structural member forcing said beams inside the sensor to be subjected to the same said repetitive cyclic movement as said structural member.

13. The method of claim 10, wherein said breakable beams are manufactured with different size notches or similarly engineered geometry in order to accelerate their fatigue process and break progressively one by one after being subjected to the different number of said repetitive cyclic bending movements.

14. The method of claim 10, wherein one or more of said breakable sensing beams inside said sensor are designed to break before an expected lifetime fatigue cycle of said structural member expires.

15. The method of claim 13, wherein a number of unbroken beams inside said sensor indicates a remaining service life of said structural member.

16. The method of claim 13, wherein said notches or similarly engineered geometry are ways of engineering a fatigue life of said breakable sensing beams which cause the beams to break after going through an engineered number of cyclic bending movements.

17. The method of claim 10, wherein a number of broken sensing beams inside said sensor is detected by electronics of said sensor and reported wirelessly to said interrogator during a service interval to indicate a remaining service life of said structural member.

18. The apparatus of claim 5, wherein said processor comprises a wireless communication tag that enables interrogation of said sensor by remote means using RFID technique or wireless sensor networking techniques.

* * * * *